United States Patent [19]

Takaishi et al.

[11] 4,229,324
[45] Oct. 21, 1980

[54] TRICYCLO-α,β-UNSATURATED ALDEHYDE

[75] Inventors: Naotake Takaishi, Ichikai; Yoshiaki Inamoto, Utsunomiya; Masamoto Matsukane, Funabashi, all of Japan

[73] Assignee: Kao Soap Company, Limited, Tokyo, Japan

[21] Appl. No.: 33,511

[22] Filed: Apr. 26, 1979

[30] Foreign Application Priority Data

May 4, 1978 [JP] Japan .................................. 53-53620

[51] Int. Cl.² ..................... C07C 45/08; C07C 47/34; A61K 7/46
[52] U.S. Cl. .................................. 252/522 R; 568/445
[58] Field of Search ..................... 260/598; 252/522 R

[56] References Cited

U.S. PATENT DOCUMENTS

| | | | |
|---|---|---|---|
| 2,880,241 | 3/1959 | Hughes | 260/598 X |
| 3,270,061 | 8/1966 | Chodroff et al. | 260/598 X |
| 4,014,938 | 3/1977 | Leidig | 260/598 |
| 4,057,515 | 11/1977 | Boelens et al. | 260/598 X |

OTHER PUBLICATIONS

Adams et al., Organic Reactions, vol. 16 (1968), 1–19 & 69–77.

*Primary Examiner*—Bernard Helfin

*Attorney, Agent, or Firm*—Oblon, Fisher, Spivak, McClelland & Maier

[57] ABSTRACT

A tricyclo-α,β-unsaturated aldehyde represented by the formula (I),

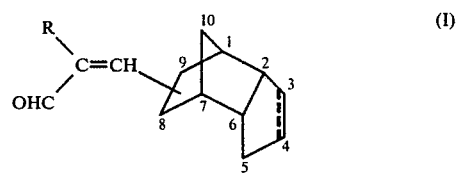

wherein the group

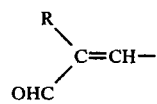

is attached to the exo side of the norbornane ring at the 8- or 9-position, R represents an alkyl group having 1 to 6 carbon atoms, and the dotted line between carbon 3 and carbon 4 represents a saturated or ethylenically unsaturated bond possesses odorous characteristics and is useful for perfume compositions.

11 Claims, No Drawings

TRICYCLO-α,β-UNSATURATED ALDEHYDE

BACKGROUND OF THE INVENTION

1. Field of the Invention

This invention relates to tricycloaldehydes. More particularly, the invention relates to a novel tricycloα,β-unsaturated aldehyde of the formula (I),

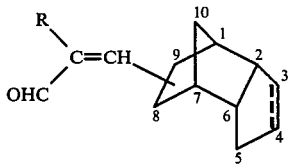

wherein the group

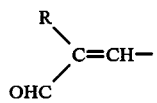

is attached to the exo side of the norbornane ring at the 8- or 9-position, R represents an alkyl group having 1 to 6 carbon atoms, and the dotted line between carbon 3 and carbon 4 represents a saturated or ethylenically unsaturated bond, and to a process for producing the aldehyde, and further to a perfume composition comprising the aldehyde.

2. Description of the Prior Art

It is known that some tricyclo [5.2.1.0$^{2,6}$]decane derivatives obtained from endo-dicyclopentadiene are useful as an odorous ingredient for perfume compositions (Japanese Patent Publication No. 49-25340 and No. 51-9014, and Japanese Laid-open Application No. 50-84558 and No. 52-70036).

The present inventors have synthesizd a wide variety of polycyclic compounds similar to sesquiterpenes, diterpenes and adamantanes and have examined their biological activities, and have found that a carbonyl group is introduced regiospecifically and stereospecifically at the 8- and 9-positon on the exo side of a norbornane ring by an oxo reaction of the endo-dicyclopentadiene in the presence of a rhodium catalyst, thereby forming 8- and 9-exo-formyl-endo-tricyclo[5.2.1.0$^{2,6}$]-deca-3-ene represented by the formulae (IIa) and (IIb) and having an aldehyde group attached to the exo side of the norbornane ring. This finding is disclosed in Synthetic Communications, 6, 199 (1976) and Japanese Laid-open Application No. 52-68168.

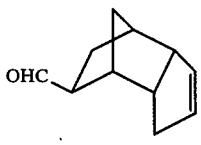
(IIa)

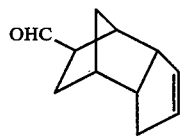
(IIb)

As a result of their continued studies concerning the above-mentioned 8-and 9-exo-formyl-endo-tricyclo[5.2.1.0$^{2,6}$]-deca-3-ene, the inventors have discovered that a tricycloα,β-unsaturated aldehyde of the formula (I) can be produced by aldol condensation of the compound of the formula (IIa), or 8-exo-formyl-endo-tricyclo[5.2.1.0$^{2,6}$]decane obtained by hydrogenating the aldehyde or compound of the formula (IIa) or (IIb), with an aliphatic aldehyde and that the compound of the formula (I) possesses a woody odor. Therefore, perfume compositions may be prepared with the use of the present compound as an odorous ingredient.

Based on this discovery, the present invention has been accomplished.

SUMMARY OF THE INVENTION

It is one object of this invention to provide a novel tricyclo-α,β-unsaturated aldehyde of the formula (I) which is useful as an odorous ingredient.

Another object of the invention is to provide a novel process for producing the compound of the formula (I).

A further object of the invention is to provide a novel perfume composition comprising the compound of the formula (I).

According to the present invention, there is provided a tricyclo-α,β-unsaturated aldehyde of the formula (I),

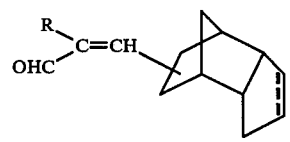

wherein the group

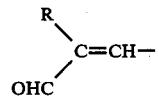

is attached to the exo side of the norbornane ring at the 8- or 9-position, R represents an alkyl group having 1 to 6 carbon atoms, and the dotted line between carbon 3 and carbon 4 represents a saturated or ethylenically unsaturated bond.

DETAILED DESCRIPTION OF THE PREFERRED EMBODIMENTS

A tricyclo-α,β-unsaturated aldehyde represented by the formula (I) of the present invention can be produced, for instance, by condensing 8- or 9-exo-formyl-endo-tricyclo[5.2.1.0$^{2,6}$]deca-3-ene or 8-exo-formyl-endo-tricyclo[5.2.1.0$^{2,6}$]decane of the formula or a mixture thereof with an aliphatic aldehyde of the formula (IV), as shown in the following

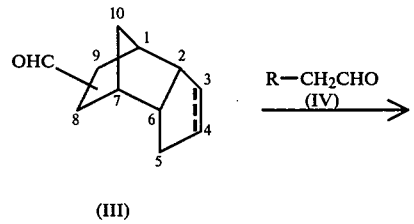

(III)

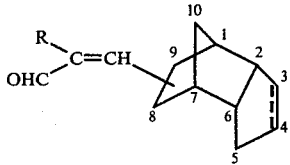

(I)

wherein the group OHC- is attached to the exo side of the norbornane ring at the 8- or 9-position, R represents an alkyl group having 1 to 6 carbon atoms, and the dotted line between carbon 3 and carbon 4 represents a saturated or ethylenically unsaturated bond.

8- or 9-Exo-formyl-endo-tricyclo[5.2.1.0$^{2,6}$]deca-3-ene may be produced by reacting endo-dicyclopentadiene (endo-tricyclo[5.2.1.0$^{2,6}$]deca-3,8diene) with carbon monoxide and hydrogen in the presence of a rhodium-triarylphosphine catalyst as disclosed in Synthetic Communications, 6 199 (1976) and Japanese Laid-open Application No. 52-68168 cited above. The rhodium-triarylphosphine catalyst includes, for example, those represented by the formulae, HRh(CO) (PR$_3$)$_3$, XRh(CO) (PR$_3$)$_2$, and XRh(PR$_3$)$_3$ wherein R is phenyl or a phenyl group substituted with an alkyl or alkoxy radical, and X is a halogen atom selected from the group consisting of chlorine, bromine and iodine. The catalyst may be used in catalytic amount, preferably in an amount of 0.01 to 1% based on endo-dicyclopentadiene. The oxo reaction is preferably carried out in an inert solvent, for example, a hydrocarbon solvent such as benzene or toluene, or in an ether solvent such as ethyl ether or tetrahydrofuran under a pressure of about 20 to 150 atm. at a temperature of about 50° to 150° C.

8-Exo-formyl-endo-tricyclo[5.2.1.0$^{2,6}$]decane (the dotted bond betwen carbon 3 and carbon 4 is saturated) which is useful as a starting material in the present invention may be produced by hydrogenating 8- and/or 9-exo-formyl-endo-tricyclo[5.2.1.0$^{2,6}$]deca-3-ene in the presence of a hydrogenation catalyst. The hydrogenation reaction is preferably carried out under a hydrogen gas pressure of 1 to 250 atm. at a temperature of room temperature to about 100° C. in an inert solution such as a hydrocarbon solvent (n-hexane or n-pentane), an aromatic hydrocarbon solvent (benzene, toluene or xylene) or an ether solvent (ethyl ether or tetrahydrofuran) with the addition of 1/10,000 to 1/100 mole per one mole of the olefin aldehyde of the formula (IIa) or (IIb) in the presence of the rhodium catalyst defined above.

Suitable alkyl groups having 1 to 6 carbon atoms in the formula (I) of the invention include, for example, methyl, ethyl, n-propyl, isopropyl, n-butyl, isobutyl, tert-butyl, n-amyl, isoamyl and tert-amyl groups.

Suitable alphatic aldehydes having the formula (IV) include, for example, propionaldehyde, n-butyr-aldehyde, n-valeraldehyde, isovaleraldehyde, hexanal and heptanal.

The reaction of this invention may be carried out in a molar ratio of 2:1 to 1:5 of the compound of the formula (III) to the aliphatic aldehyde of the formula (IV), preferably in a molar ratio of about 1:1. For the best results, the reaction is conducted with refluxing under strongly basic conditions. Suitable strong bases include, for example, sodium hydroxide, potassium hydroxide and a strongly basic ion exchange resin.

Because of its characteristic, long-lasting odor, the compound of the formula (I) according to the invention is an excellent odorous ingredient in the manufacture of perfume compositions for such industrial products as detergents, cleansers, cosmetics, soaps, shampoos, perfumes and like carriers.

The invention is now described in further detail with reference to some non-limiting Examples.

EXAMPLE 1

Preparation of a mixture of 8- and 9-exo-formyl-endo-tricyclo[5.2.1.0$^{2,6}$]deca-3-ene:

66 Grams of endo-dicyclopentadiene (0.5 mole), 100 ml of benzene, 345 mg of RhCl(CO)(PPh$_3$)$_2$ and 0.25 ml of triethyl amine where charged into an autoclave. The air in the autoclave was replaced with carbon monoxide gas, and a carbon monoxide-hydrogen gas mixture having a molar ratio of 1:1 was then introduced into the reaction mixture under a pressure of 100 atm. at 70° C. until an equivalent gas mixture was absorbed. After cooling, the solvent was removed from the reaction mixture, and the residue was distilled to obtain 66.4 g (yield: 82%) of the above tricyclo-α,β-unsaturated aldehyde in the form of an oily mixture.

EXAMPLE 2

Preparation of 8-exo-formyl-endo-tricyclo[5.2.1.0$^{2,6}$]-decane:

100 Grams of a mixture of 8- and 9-exo-formyl-endo-tricyclo[5.2.1.0$^{2,6}$]deca-3-ene, 1 g of tris-triphenylphosphine rhodium chloride and 150 ml of benzene were charged into an autoclave. Hydrogen gas was introduced into the mixture under a presure of 50 atm. at a temperature of 50° C. until the absorption of the hydrogen gas ceased. After the completion of the reaction, the benzene was removed under reduced pressure to obtain 91.6 g (yield: 90%) of the above tricyclo-α,β-unsaturated aldehyde.

Elemental Analysis as $C_{11}H_{16}O$:
Calculated (%): C 80.8, H 9.6
Found (%): C 80.5, H 9.8
Boiling Point: 78 C/1.9 mmHg
IR (neat): cm$^{-1}$ 2950, 2860, 2800, 2700, 1720, 1450, 1050.
NMR (CDCl$_3$ solvent, TMS internal standard): 1.2–2.7 (multiplet), 9.8 (CHO, singlet)
MS: m/e (relative intensity) 164 (M+, 6) 135 (65), 108 (25), 107 (60), 106 (16), 93 (19), 81 (16), 79 (29), 67 (100), 41 (39), 39 (24).

EXAMPLE 3

Preparation of a mixture of 2-methyl-3-(endo-tricyclo[5.2.1.0$^{2,6}$]deca-3-ene-8-exo-yl)-propa-2-ene-1-al and 2-methyl-3-(endo-tricyclo[5.2.1.0$^{2,6}$]deca-3-ene-9-exo-yl)-propa-2-ene-1-al:

To a mixture of 2.0 g (0.012 mole) of an admixture of 8-exo-formyl-endo-tricyclo[5.2.1.0$^{2,6}$]deca-3-ene and 9-exo-formyl-endo-tricylo[5.2.1.0$^{2,6}$]deca-3-ene, 2.1 g (0.037 mole) of propionaldehyde and 10 ml of methanol was added with stirring 0.5 ml of an aqueous solution containing 40% sodium hydroxide, and the resulting mixture was refluxed for 2 hours. After the completion of this reaction, the methanol was removed from the reaction mixture by distillation, and 100 ml of ethyl ether and 50 ml of water were added to the residue. Thereafter, the organic layer was separated, and the aqueous solution was extracted with ether. After being combined and washed with water, both the extract and the organic layer were dried over anhydrous sodium sulfate, concentrated and fractionated to yield 1.94 g (yield: 80%) of the above tricyclo-α,β-unsaturated aldehyde mixture having a boiling point of 100° to 102° C./1 mmHg.

Elemental Analysis as $C_{14}H_{18}O$:
Calculated (%): C 83.12, H 8.97.
Found (%): C 83.28, H 8.85.
$\eta_D^{20}$: 1.5389
IR: 3020, 1680, 1630 cm$^{-1}$.

A perfume composition comprising the product thus obtained possess a woody-orris odor.

EXAMPLE 4

Preparation of 2-methyl-3-(endo-tricyclo[5.2.1.0$^{2,6}$]-deca-8-exo-yl)-propa-2-ene-1-al:

The same procedure was repeated as in Example 1, except that 2.0 g (0.012 mole) of 8-exo-formyl-endo-tricyclo[5.2.1.0$^{2,6}$]decane was used instead of an admixture of 8-exo-formyl-endo-tricyclo[5.2.1.0$^{2,6}$]deca-3-ene and 9-exo-formyl-endo-tricyclo[5.2.1.0$^{2,6}$]deca-3-ene, thereby obtaining 2.1 g (yield: 85%) of the above tricyclo-α,β-unsaturated aldehyde having a boiling point of 105° to 106° C./1 mm Hg.

Elemental Analysis as $C_{14}H_{20}O$:
Calculated (%): C 82.30, H 9.87.
Found (%): C 82.58, H 9.69.
$\eta_D^{20}$: 1.5302
IR: 1680, 1630 cm$^{-1}$.

A perfume composition comprising the product thus obtained possesses a woody-orris odor.

EXAMPLE 5

Preparation of a mixture of 2-ethyl-3-(endo-tricyclo[5.2.1.0$^{2,6}$]deca-3-ene-8-exo-yl)-propa-2-ene-1-al and 2-ethyl-3-(endo-tricyclo[5.2.1.0$^{2,6}$]deca-3-ene-9-exo-yl)-propa-2-ene-1-al:

The same procedure was repeated as in Example 1, except that 2.67 g (0.037 mole) of n-butyraldehyde was used instead of propionaldehyde, thereby obtaining 2.13 g (yield: 82%) of the above tricyclo-α,β-unsaturated aldehyde mixture having a boiling point of 105° to 106° C./1 mmHg.

Elemental Analysis as $C_{15}H_{20}O$:
Calculated (%): C 83.29, H 9.32.
Found (%): C 83.19, H 9.55.
$\eta_D^{20}$: 1.5288.
IR: 3025, 1685, 1630 cm$^{-1}$.

A perfume composition comprising the product thus obatined possesses a woody, honey odor.

EXAMPLE 6

Preparation of 2-ethyl-3-(endo-tricyclo[5.2.1.0$^{2,6}$]-deca-8-exo-yl)-propa-2-ene-1-al:

The same procedure was repeated as in Example 1, except that 2.0 g (0.012 mole) of 8-exo-formyl-endo-tricyclo[5.2.1.0$^{2,6}$]decane and 2.67 g (0.037 mole) of n-butyraldehyde were used, thereby obtaining 2.1 g (yield 80%) of the above tricyclo-α,β-unsaturated aldehyde having a boiling point of 105° to 106° C./1 mmHg.

Elemental Analysis as $C_{15}H_{22}O$:
Calculated (%): C 82.52, H 10.16.
Found (%): C 82.75, H 10.12.
$\eta_D^{20}$: 1.5172.
IR: 1690, 1640 cm$^{-1}$.

A perfume composition comprising the product thus obtained possesses a woody, honey odor.

What is claimed is:

1. An endo-tricyclo-α,β-unsaturated aldehyde represented by the formula (I),

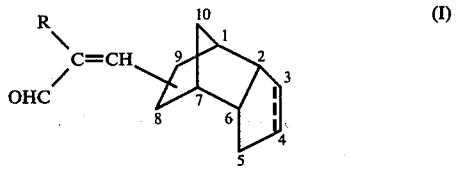

wherein the group

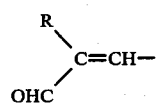

is attached to the exo side of the norbornane ring at the 8- or 9-position, R represents an alkyl group having 1 to 6 carbon atoms, and the dotted line between carbon 3 and carbon 4 represents a saturated or ethylenically unsaturated bond.

2. The tricyclo-α,β-unsaturated aldehyde according to claim 1, wherein the alkyl group in the formula (I) is selected from the group consisting of methyl, ethyl, n-propyl, isopropyl, n-butyl, isobutyl, tert-butyl, n-amyl, isoamyl and tert-amyl groups.

3. A process for producing an endo-tricyclo-α,β-unsaturated aldehyde represented by the formula (I),

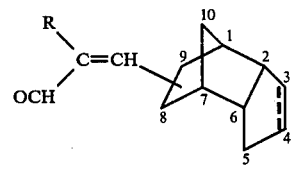

wherein the group

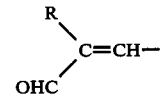

is attached to the exo side of the norbornane ring at the 8- or 9-position, R represents an alkyl group having 1 to 6 carbon atoms, and the dotted line between carbon 3 and carbon 4 represents a saturated or ethylenically unsaturated bond, which comprises reacting 8- or 9-exo-formyl-endo-tricyclo[5.2.1.0$^{2,6}$]deca-3-ene or 8-exo-formyl-endo-tricyclo[5.2.1.0$^{2,6}$]decane represented by the formula (III),

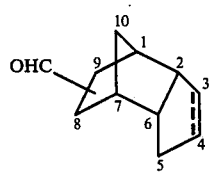

wherein the group OHC— is attached to the exo side of the norbornane ring at the 8- or 9-position, and the dotted line between carbon 3 and carbon 4 represents a saturated or ethylenically unsaturated bond, or a mixture thereof, with an aliphatic aldehyde represented by the formula (IV),

  R—CH₂CHO                                    (IV)

wherein R is the same as defined above.

4. The process according to claim 3, wherein said alkyl group in the formula (I) selected from the group consisting of methyl, ethyl, n-propyl, isopropyl, n-butyl, isobutyl, tert-butyl, n-amyl, isoamyl and tert-amyl groups.

5. The process according to claim 3, wherein said aliphatic aldehyde is selected from the group consisting of propionaldehyde, n-butylaldehyde, n-valeraldehyde, isovaleraldehyde, hexanal and heptanal.

6. The process according to claim 3, wherein the reaction is carried out in a molar ratio of 2:1 to 1:5 of 8- or 9-exo-formyl-endo-tricyclo[5.2.1.0²,⁶]deca-3-ene or 8-exo-formyl-endo-tricyclo[5.2.1.0²,⁶]decane, or a mixture thereof to aliphatic aldehyde.

7. The process according to claim 3, wherein the reaction is conducted under refluxing conditions.

8. The process according to claim 3, wherein the reaction is carried out in the presence of a strong base selected from the group consisting of sodium hyroxide, potassium hydroxide and a strongly basic ion exchange resin.

9. A process for producing a tricyclo-α,β-unsaturated aldehyde represented by the formula (V),

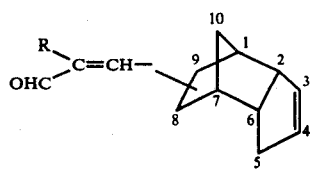                                               (V)

wherein the group

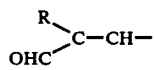

is attached to the exo side of the norbornane ring at the 8- or 9-position, and R represents an alkyl group having 1 to 6 carbon atoms, which process comprises:
  (a) reacting endo-dicyclopentadiene with carbon monoxide and hydrogen in the presence of a rhodiumtriarylphosphine catalyst to obtain 8- or 9-exo-formyl-endo-tricyclo[5.2.1.0²,⁶]deca-3-ene, and
  (b) condensing said 8- or 9-exo-formyl-endo-tricyclo[5.2.1.0²,⁶]deca-3-ene with an aliphatic aldehyde represented by the formula (IV),

  R—CH₂CHO                                    (IV)

wherein R is the same as defined above.

10. A process for producing a endo-tricyclo-α,β-unsaturated aldehyde represented by the formula (VI),

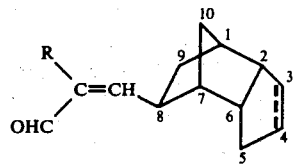                                               (VI)

wherein the group

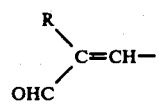

is attached to the exo side of the norbornane ring at the 8-position, and R represents an alkyl group having 1 to 6 carbon atoms, which process comprises:
  (a) reacting endo-dicyclopentadiene with carbon monoxide and hydrogen in the presence of a rhodiumtriarylphosphine catalyst to obtain 8- or 9-exo-formyl-endo-tricyclo[5.2.1.0²,⁶]deca-3-ene,
  (b) hydrogenating said 8- or 9-exo-formyl-endo-tricyclo[5.2.1.0²,⁶]deca-3-ene in the presence a hydrogenation catalyst to obtain 8-exo-formyl-endo-tricyclo[5.2.1.0²,⁶]decane, and
  (c) condensing said 8-exo-formyl-endo-tricyclo[5.2.1.0²,⁶]decane with an aliphatic aldehyde represented by the formula (IV),

  R—CH₂CHO                                    (IV)

wherein R is the same as defined above.

11. A perfume composition comprising an endo-tricyclo-α,β-unsaturated aldehyde represented by the formula (I),

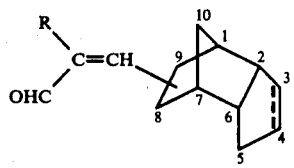                                                (I)

wherein the group

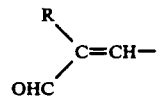

is attached to the exo side of the norbornane ring at the 8- or 9-position, R represents an alkyl group having 1 to 6 carbon atoms, and the dotted line between carbon 3 and carbon 4 represents a saturated or ethylenically unsaturated bond.

* * * * *